United States Patent [19]

Sears

[11] 4,426,330

[45] Jan. 17, 1984

[54] SYNTHETIC PHOSPHOLIPID COMPOUNDS

[75] Inventor: Barry D. Sears, Marblehead, Mass.

[73] Assignee: Lipid Specialties, Inc., Cambridge, Mass.

[21] Appl. No.: 284,675

[22] Filed: Jul. 20, 1981

[51] Int. Cl.$^3$ .............................................. C07F 9/02
[52] U.S. Cl. .................................................. 260/403
[58] Field of Search ........................................ 260/403

[56] References Cited

U.S. PATENT DOCUMENTS

| | | | |
|---|---|---|---|
| 2,310,679 | 2/1943 | De Groote et al. | 260/403 X |
| 3,085,100 | 4/1963 | Chang | 260/403 |
| 3,542,820 | 11/1970 | Rakhit | 260/403 |
| 3,577,446 | 5/1971 | Rakhit | 260/403 |
| 4,016,100 | 4/1977 | Suzuki et al. | 252/316 |
| 4,086,257 | 4/1978 | Sears | 260/403 |
| 4,159,988 | 7/1979 | Eibl et al. | 260/403 X |
| 4,261,911 | 4/1981 | Lindemann et al. | 260/403 |

FOREIGN PATENT DOCUMENTS 2756866  6/1979  Fed. Rep. of Germany ...... 260/403
727655  4/1980  U.S.S.R. .............................. 260/403

OTHER PUBLICATIONS

Wren et al., CA 63: 13066 (1965).
Rehbinder et al., *Index Chemicus*, 17, 50791 (1965).
Szogyi et al., CA 96: 129747k (1982).

*Primary Examiner*—Thomas A. Waltz
*Attorney, Agent, or Firm*—Richard P. Crowley

[57] ABSTRACT

Novel synthetic phospholipid compounds, the compounds having the structural formula:

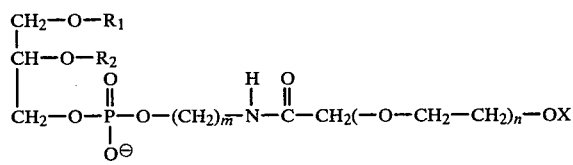

where X is a hydrogen or alkyl group, n can vary from about 0 to 200, m can vary from 2 to 10, and $R_1$ and $R_2$ are saturated or unsaturated acyl radicals.

9 Claims, No Drawings

SYNTHETIC PHOSPHOLIPID COMPOUNDS

BACKGROUND OF THE INVENTION

Phospholipids, such as lecithin, are amphipathic compounds in that they consist of both hydrophobic and hydrophilic groups or regions within the same molecule. The balance between these hydrophobic and hydrophilic regions determines their physical properties in an aqueous environment. The uses of natural phospholipids as additives are numerous in the food industry (e.g., as emulsifiers), in cosmetics, for industrial uses, and for the pharmaceutical industry, especially in the preparation of drug-delivery systems. U.S. Pat. Nos. 4,086,257, 4,097,502, 4,097,503, 4,145,410 and 4,159,988 disclose various modifications of the polar-head-group region of natural phospholipids which lead to unique and unexpected physical properties.

Further, various derivatives of lecithin are known, such as, for example, oxyalkylated lecithin compounds (see U.S. Pat. Nos. 2,310,679 and 3,085,100), and phosphatidyl-alkanolamine derivatives (see for example U.S. Pat. Nos. 2,801,255, 3,542,820, 3,577,446 and 4,254,115). It is desirable to provide novel synthetic phospholipids, particularly having enhanced, controlled, solubility properties in an aqueous environment.

SUMMARY OF THE INVENTION

This invention relates to phospholipid compounds, to the method of preparing the phospholipid compounds and to the use of the phospholipid compounds, particularly in an aqueous environment. More particularly, this invention concerns novel synthetic phosphatidyl polyethylene oxide compounds, their preparation and their use to encapsulate drugs in a drug-delivery system.

This invention describes a new series of phospholipid compounds in which the polar-head-group region is modified by the covalent attachment of polyalkylene oxide polymers of various molecular weights. These phospholipid compounds have the following structural formula:

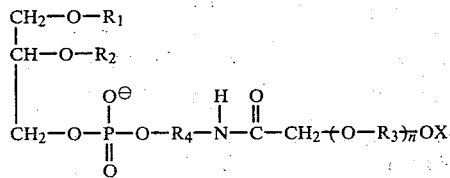

where $R_1$ and $R_2$ represent hydrogen or saturated or unsaturated straight-chain or branched-chain acyl groups and where $R_3$ represents an alkylene group, particularly, but not limited to, ethylene, propylene and mixtures thereof, and $R_4$ represents a $C_2$-$C_{10}$ group, particularly an ethylene group -$CH_2CH_2$- as in natural lecithin or a trismethylene (propylene) to decamethylene group. The number of alkylene oxide groups in the polymer, designated as n, may vary from 0 to about 200 or more; e.g., 10–100, such as 3–20. X is a hydrogen or alkyl group, such as a $C_1$-$C_4$ group like methyl. The attachment of the relatively hydrophilic polyalkylene oxide polymer, particularly the polyethylene oxide, alters the hydrophilic to hydrophobic balance within the phospholipid, in order to give unique solubility properties to the phospholipid compound in an aqueous environment.

The novel synthetic phospholipid compounds have the structural formula:

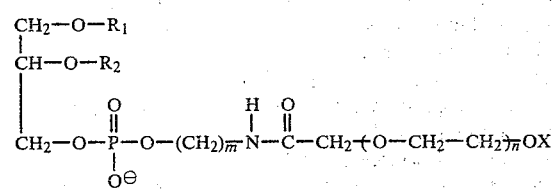

where X is hydrogen or a methyl group, n can vary from about 0 to 200, m can vary from 2 to 10, and $R_1$ and $R_2$ are saturated or unsaturated acyl radicals.

These novel compounds have a distinctly different chemical composition than the compounds described, for example, in U.S. Pat. Nos. 2,310,679 and 3,085,100, which are products from the coupling of ethylene oxide or similar compounds to crude soy "lecithin". The use of the term "lecithin" describes a number of compounds including lecithin (i.e., phosphatidylcholine), a compound that cannot react with ethylene oxide. On the other hand, soy "lecithin" does contain phosphatidylethanolamine, phosphatidylinositol, and a variety of glycolipids. All of these compounds in crude "lecithin" can react with ethylene oxide or similar compounds containing a reactive cyclo oxide group to form various adducts. For example, in phosphatidylinositol and with glycolipids, the reactive groups in these molecules are hydroxyl groups which will form an ether linkage when reacted with ethylene oxide. Phosphatidylethanolamine, which contains a primary amino group, will react with ethylene oxide to form an alkylamine linkage (see N. Schonfeldt, "Surface Active Ethylene Oxide Adducts" Pergamon Press, 1969). In both cases, these adducts should not be biologically degradable, and, therefore, such compounds will be undesirable for the use in the cosmetic and pharmaceutical industries.

The phospholipids of the invention comprise synthetic phospholipids in which the linkage between the synthetic ethylene oxide or propylene oxide polymer and the naturally occurring phospholipid is a biologically degradable linkage; e.g., an amide linkage, which makes these novel phospholipid compounds useful for cosmetics and pharmaceutical uses.

The preparation of these compounds is best accomplished by the coupling of the appropriate carboxylic analog of the polyalkylene oxide polymer to the phosphatidylalkanolamine molecule, such as the phosphatidyethanolamine molecule, for example, a polyethylene oxide polymer analog having the structure:

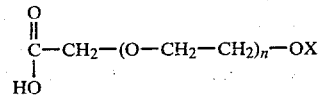

where X is a hydrogen or alkyl group and where n can vary from 0 to about 200. The carboxylic analog of the polyethylene oxide polymer can be prepared by using either $KMnO_4$ or pyridium dichromate or other oxidizing agent, to oxidize a suitable polyalkylene oxide polymer starting material as shown below:

$$OH-CH_2-CH_2-(O-CH_2-CH_2)_n-OX$$

The oxidized compound is then further purified via distillation and ion-exchange chromatography. The carboxylic analog of the polyethylene oxide polymer is activated by a convenient activating agent, such as oxalyl chloride or 1,1 carbonyl diimidazole. The activated carboxylic derivative of the parent polyethylene oxide polymer is then coupled to the phosphatidylethanolamine via an amide linkage, to form the phospholipid analog compounds of the invention.

The phosphatidylethanolamine or synthetic analogs of phosphatidylethanolamine can either be isolated from natural sources, synthesized according to established chemical procedures, or enzymatically synthesized using the corresponding phosphatidyl choline compound in the presence of ethanolamine and phospholipase D. The $R_1$ and $R_2$ can range from straight or branched carbon acyl radicals ranging from 2 to 24 carbon atoms; e.g., $C_2$–$C_{20}$, or the corresponding acyl radicals of unsaturated fatty acids, such as, but not limited to, oleic, stearic, linoleic, linolenic, palmitic, myristic, or arachidonic acids.

The reaction of the phosphatidylethanolamine and the carboxylic derivative of the polyethylene oxide polymer is carried out in an inert solvent, such as dry benzene. The progress of the reaction can be monitored by thin-layer chromatography. Purification of the final product, if necessary, may be carried out using column chromatography.

In the phospholipid compounds of the invention, the polar head group of the phosphatidylethanolamine has been modified to alter their physical properties, by the inclusion of a polyalklene oxide polymer. In all cases where natural phospholipids can be used, such as in drug-delivery systems, in cosmetics, in food and industrial uses, in treating atherosclerosis, for intravenous nutrition, and other uses, these new synthetic phospholipid compounds can be used alone or in combination with other natural phospholipids, especially phosphatidyl choline. Biologically these synthetic phospholipids will be physiologically inert. For example as polyethylene oxide polymers attached to proteins are nonimmunogenic and well tolerated by the body (see Abuchowski et al. J. Biol. Chem. 252, pp. 3578–3581 (1977)). The covalent linkage between the polyethylene oxide polymer and the phosphatidylethanolamine is biologically degradable, and phosphatidylethanolamine, itself, is a natural compound.

As a result, these novel compounds will have great utility in encapsulating drugs as drug-delivery systems that can either be administered orally or via injection, such as in the encapsulation process disclosed in corresponding U.S. Ser. No. 90,994, filed Nov. 13, 1979, now U.S. Pat. No. 4,320,121, issued Mar. 16, 1982, as well as in the method of U.S. Pat. No. 4,016,100, both hereby incorporated by reference herein.

The presence of the hydrophilic alkylene oxide polymer, particularly the polyethylene oxide polymer moiety in these new phospholipids, also gives rise to novel and unexpected physical properties in an aqueous environment. Unsaturated phosphatidylethanolamines, especially those isolated from soy beans, do not form any stable type of structure in water. On the other hand, although gangliosides have a similar hydrophobic region compared to phosphatidylethanolamine, the polar region of the ganglioside molecule is composed of hydrophilic oligiosaccahrides. The presence of these oligiosaccahrides allows the ganglioside to organize into a stable micelle upon hydration with water. By covalently attaching a hydrophilic polymer, such as polyethylene oxide polymers, to phosphatidylethanolamine, phospholipid analog to ganglioside is essentially synthesized. It should also be noted that, while no molecular species of phosphatidylethanolamine will form a stable structure in an aqueous environment, the phospholipid analog compounds described herein do form stable structures upon hydration.

The actual organization of these structures, however, will depend at least in part on the selected acyl chain composition of the phosphatidylethanolamine and the length of the alkylene oxide polymer. Moreover, the combination of these new phospholipid analogs with natural phospholipids, especially in small sonicated phospholipid vesicles, will stabilize these vesicles which are naturally unstable. This stabilization may occur by the presence of the polyalkylene oxide polymer which may act as a physical barrier that prevents vesicle-vesicle contact that might result in the subsequent coalescence of the sonicated phospholipid vesicles.

This invention will be described for the purpose of explanation and illustration only in connection with the preparation of certain preferred composition; however, it is recognized and is within the scope and intent of my invention and disclosure that other compounds and method of preparation can be formulated and used.

DESCRIPTION OF THE EMBODIMENTS

Example 1

1120 μmoles of soy phosphatidylethanolamine were taken to dryness under high vacuum. 4480 μmoles of monomethyl polyethylene oxide carboxylic derivative (average molecular weight of 134) and 2240 μmoles of 1,1 carbonyl diimidazole were mixed in 5 ml. of dry benzene. The solution was heated to 40° C. until the bubbling ceased. This solution was added to the dry phospholipid and the final volume was reduced to 3 ml. and heated for 3 hours at 65° C. Thin-layer chromatography indicated a complete reaction. The product was purified by silicic acid chromatography. The final yield of the purified product was 74%. The product has a $R_f$ of 0.46 in a solvent system composed of 75/25/1 ($CHCl_3$/methanol/$NH_4OH$). In the same solvent system, phosphatidylethanolamine had an $R_f$ of 0.14.

Example 2

1120 μmoles of purified soy phosphatidylethanolamine were taken to dryness under high vacuum. 1680 μmoles of the monomethyl polyethylene oxide carboxylic derivative (average molecule weight 1900) and 1400 μmoles of 1,1 carbonyl diimidazole were dissolved in 10 ml. of dry benzene. The solution was heated at 40° C. until the bubbling had ceased. The mixture was then added to the dry phospholipid and the total volume was reduced to 5 ml. and heated for 3 hours at 65° C. The product was purified by silicic acid chromatography to give an overall yield of 7%. The $R_f$ of the product in the same solvent system as in Example 1 was 0.78.

Example 3

800 μmoles of purified soy phosphatidylethanolamine was taken to dryness under high vacuum. 2400 μmoles of monomethyl polyethylene oxide carboxylic derivative (average molecular weight 266) were dissolved in 11 ml. of dry benzene, and 2160 μmoles of 1,1 carbonyl diimidazole were added and the solution was heated at 40° C. until the bubbling had ceased. The solution was added to the dried phospholipid and the volume was reduced to 3 ml. The reaction was heated at 65° C. for 3 hours. The product was purified by silicic acid chromatography to give a yield of 34%. The $R_f$ of the product in the same solvent system as in Example 1 was 0.62.

Example 4

491 μmoles of soy phosphatidylethanolamine were taken to dryness under high vacuum. 1560 μmoles of methoxyacetic acid and 1560 μmoles of 1,1 carbonyl diimidazole were dissolved in 10 ml. of dry benzene and heated at 40° C. until the bubbling had ceased. The solution was added to the dry phosphatidylethanolamine and the volume was reduced to 3 ml. The solution was heated to 60° C. for 3 hours. Thin-layer chromatography indicated a complete reaction. The product was extracted with a Folch extraction system and the lower phase was taken to dryness. The yield was 92%. The $R_f$ of the compound in the same solvent as in Example 1 was 0.44.

Example 5

1120 μmoles of soy phosphatidylethanolamine were taken to dryness under high vacuum. 3360 μmoles of monomethyl polyethylene oxide carboxylic derivative (average molecular weight 224) and 2240 μmoles of 1,1 carbonyl diimidazole were dissolved in 10 ml. of dry benzene and heated at 40° C. until the bubbling had ceased. The solution was added to the dry phospholipid and the volume was reduced to 3 ml. The solution was heated for 3 hours at 70° C. The product was purified by silicic acid chromatography. The yield of the product was 53%. The $R_f$ of the product in the same solvent systems in Example 1 was 0.61.

What I claim is:

1. A phosphatidyl alkylene oxide compound having the structural formula:

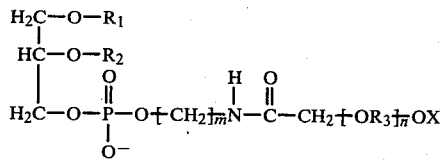

where $R_1$ and $R_2$ are hydrogen or $C_2$–$C_{24}$ organic acyl radicals; $R_3$ is a $C_2$–$C_3$ alkylene radical, X is hydrogen or an alkyl radical, n is a number of from 0 to about 200, and m is a number of from 2 to 10.

2. The compound of claim 1 wherein $R_1$ and $R_2$ are $C_8$–$C_{20}$ fatty acid radicals.

3. The compound of claim 1 wherein n is a number of from about 10 to 100.

4. The compound of claim 1 wherein m is two.

5. The compound of claim 1 wherein X is a methyl radical.

6. The compound of claim 1 wherein $R_3$ is an ethylene radical.

7. The compound of claim 1 wherein X is hydrogen, $R_3$ is an ethylene radical, n is a number of from 10 to 100, and m is two.

8. The compound of claim 1 wherein the $R_1$ to $R_2$ radicals are derived from soy bean.

9. A phosphatidyl polyethylene oxide compound having the structural formula:

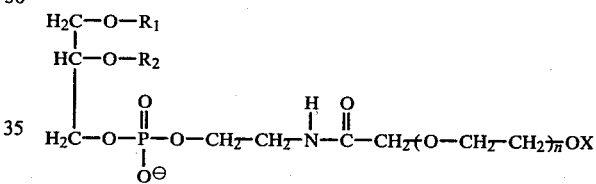

wherein $R_1$ and $R_2$ are hydrogen or $C_8$–$C_{20}$ fatty acid radicals, and n is a number from 0 to abouut 200, and X is hydrogen or alkyl group.

* * * * *